United States Patent [19]

Fuso et al.

[11] Patent Number: 5,786,475

[45] Date of Patent: Jul. 28, 1998

[54] UV ABSORBERS, THEIR PREPARATION AND THE USE THEREOF

[75] Inventors: Francesco Fuso, Therwil; Gerhard Reinert, Allschwil, both of Switzerland

[73] Assignee: Ciba Specialty Chemicals Corporation, Tarrytown, N.Y.

[21] Appl. No.: 526,860

[22] Filed: Sep. 11, 1995

[30] Foreign Application Priority Data

Sep. 14, 1994 [CH] Switzerland .............................. 2802/94

[51] Int. Cl.⁶ ...................... C07D 403/00; C07D 251/02; C07D 251/42
[52] U.S. Cl. ........................... 544/198; 544/207; 544/209; 544/211; 544/212
[58] Field of Search ................................... 544/212, 211, 544/207, 198, 209; 564/155

[56] References Cited

FOREIGN PATENT DOCUMENTS

94/04515  3/1994  WIPO .

OTHER PUBLICATIONS

Chem. Abstract, 116 : 1537725 (1992).

*Primary Examiner*—Mukund J. Shah
*Assistant Examiner*—Bruce Kifle
*Attorney, Agent, or Firm*—Kevin T. Mansfield; David R. Crichton

[57] ABSTRACT

The invention relates to compounds of formula

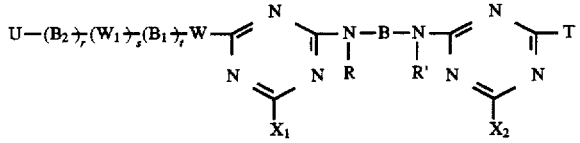

wherein the variables have the meanings given in the claims. The compounds are suitable for use as UV absorbers for the photochemical stabilization of undyed, dyed or printed textile fiber materials and for enhancing the sun protection factor thereof.

12 Claims, No Drawings

UV ABSORBERS, THEIR PREPARATION AND THE USE THEREOF

The present invention relates to novel fibre-reactive UV absorbers, to a process for their preparation and to the use thereof for the photocemical stabilisation of undyed and dyed textile fibres and for enhancing the sun protection factor of such textile fibres.

That UV radiation is harmful to the skin is known. Protection against strong solar radiation is usually afforded by applying a composition that contains a UV absorber (sun cream) direct to the skin. In particularly sunny parts of the world, as in Australia and America, there has recently been a drastic increase in the incidence of skin damage induced by UV radiation. In these countries, increased attention is hence being paid to the problem of protecting the skin from solar radiation.

The proposal has been made not just to protect the skin direct, but also to provide clothing surrounding the skin as well as textile sun protective articles such as marquees or sunshades with additional protection against UV radiation. Most natural and synthetic textile fabrics, whether undyed or dyed, are usually at least partially permeable to UV radiation, so that the mere wearing of clothing does not afford adequate protection of the skin from damage induced by UV radiaton. Remedy is possible here by incorporating UV absorbers in textile fabric.

The results obtained in the field of textile materials, especially materials containing cellulosic fibres or natural or synthetic polyamide fibres, with respect to protection from UV radiation, have so far not been satisfactory, and there is a need to develop novel UV absorbers specially tailored to these materials.

Accordingly, the invention relates to compounds of formula

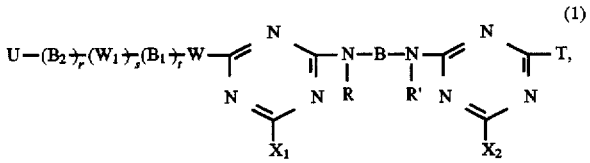

wherein

B is an aliphatic, cycloaliphatic, aromatic or aromatic-aliphatic linking group or, together with —NR— and —NR'—, forms a heterocyclic ring, $B_1$ and $B_2$ are each independently of the other an aliphatic linking group, R, R' and $R_2$ are each independently of one another hydrogen or unsubstituted or substituted $C_1$–$C_4$alkyl, U is the radical of a UV absorber, W is —$NR_2$—, —O— or —S—, $W_1$ is a radical —C(O)O—, —O(O)C—, —C(O)NH— or —HN(O)C—, $X_1$ and $X_2$ are each independently of the other halogen, hydroxy, unsubstituted or substituted amino, 3-carboxypyridin-1-yl or 3-carbamoylpyridin-1-yl, T independently has one of the meanings given for $X_1$ or is an alkoxy, aryloxy, alkylthio or arylthio radical which may be further substituted or is a nitrogen-containing heterocyclic radical or is independently a radical U—$(B_2)_r$—$(W_1)_s$—$(B_1)_t$—W—, wherein U, $B_1$, $B_2$, W and $W_1$ are each as defined above, and r, s and t are each independently of one another 0 or 1, and s is 0 when t is 0, with the proviso that the compounds of formula (1) contain at least one sulfo or sulfato group and at least one group which is removable under alkaline conditions.

B defined as an aliphatic linking group may typically be straight-chain or branched $C_2$–$C_{12}$alkylene which is unsubstituted or substituted by hydroxy, sulfo or sulfato and/or interrupted by —O—. Preferably B is straight-chain or branched $C_2$–$C_6$alkylene which is unsubstituted or substituted by hydroxy, sulfo or sulfato. Illustrative examples of particularly preferred alkylene radicals B are 1,2-ethylene, 1,2-propylene, 1,3-propylene, 2-hydroxy-1,3-propylene, 1,4-butylene, 2-methyl-1,5-pentylene and 1,6-hexylene.

B in the significance of a cycloaliphatic linking group may suitably be cyclohexylene or the radical of formula

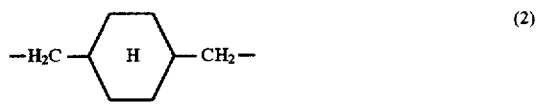

or —NR— and —NR'—, together with B, form a ring, typically a piperazino ring.

Illustrative examples of aromatic linking groups B are 1,2-, 1,3- or 1,4-phenylene, each unsubstituted or substituted by, typically, sulfo, carboxy, $C_1$–$C_4$alkyl, $C_1$–$C_4$alkoxy or halogen, unsubstituted or sulfo-substituted naphthylene or a radical of formula

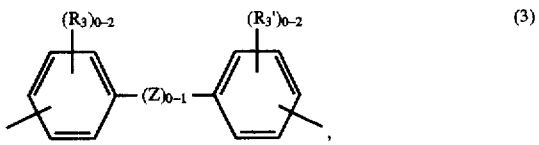

wherein Z is —CO—, —NHCO—, —NHCONH—, —$(CH_2)_{1-4}$—, —NH—, —CH=CH—, —O—, —$SO_2$— or —N=N—, and $(R_3)_{0-2}$ and $(R_3')_{0-2}$ are each independently of the other from 0 to 2 identical or different radicals selected from the group consisting of sulfo, methyl, methoxy and chloro.

A preferred aromatic linking group B is 1,3- or 1,4-phenylene, each unsubstituted or substituted by sulfo, carboxy, chloro, methyl or methoxy, naphthylene which is substituted by 1 or 2 sulfo groups, or is a radical of formula

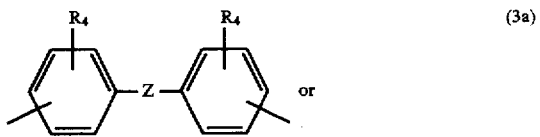

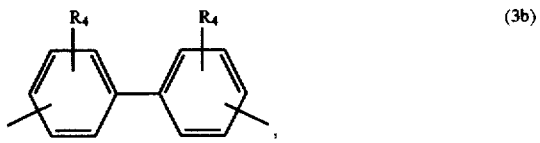

wherein Z is —NHCONH—, —O—, —NH—, —CH=CH— or —$CH_2$—, and $R_4$ is hydrogen or sulfo.

Illustrative examples of particularly preferred aromatic linking groups B are 1,3-phenylene, 1,4-phenylene, 4-methyl-1,3-phenylene, 4-sulfo-1,3-phenylene, 3-sulfo-1,4-phenylene, 3,6-disulfo-1,4-phenylene, 4,6-disulfo-1,3-phenylene, 3,7-disulfo-1,5-naphthylene, 4,8-disulfo-2,6-naphthylene, 2,2'-disulfo-4,4'-diphenylene, 4,4'-phenyleneurea-2,2'-disulfonic acid or 2,2'-disulfo-4,4'-stilbenylene. Among these groups, 4-sulfo-1,3-phenylene, 3-sulfo-1,4-phenylene, 3,6-disulfo-1,4-phenylene or 4,6-disulfo-1,3-phenylene are very particularly preferred.

Illustrative examples of aromatic-aliphatic linking groups B are phenylene-$C_1$–$C_4$alkylene which is unsubstituted or substituted in the phenylene moiety by sulfo, methyl, methoxy, carboxy or chloro. B in the significance of an aromatic-aliphatic linking group is preferably phenylenemethylene which is unsubstituted or substituted in the phenylene moiety by sulfo, methyl or methoxy.

B is preferably $C_2$–$C_6$alkylene which is unsubstituted or substituted by hydroxy, sulfo or sulfato, 1,3- or 1,4-phenylene which is unsubstituted or substituted by sulfo, carboxy, chloro, methyl or methoxy, naphthylene which is substituted by 1 or 2 sulfo groups, or is a radical of formula

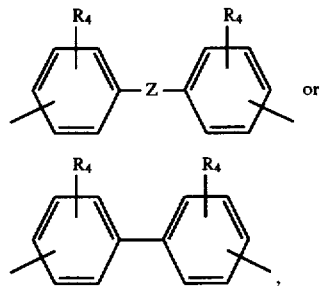

wherein Z is —NHCONH—, —O—, —NH—, —CH=CH— or —CH$_2$—, and $R_4$ is hydrogen or sulfo.

Most preferably B is 4-sulfo-1,3-phenylene, 3-sulfo-1,4-phenylene, 3,6-disulfo-1,4-phenylene or 4,6-disulfo-1,3-phenylene.

$B_1$ or $B_2$ as an aliphatic linking group may typically be straight-chain or branched $C_1$–$C_{12}$alkylene and, preferably, straight-chain or branched $C_1$–$C_6$alkylene. Illustrative examples of particularly preferred alkylene radicals $B_1$ and $B_2$ are methylene, 1,2-ethylene, 1,2-propylene 1,3-propylene, 1,4-butylene, 2-methyl-1,5-pentylene and 1,6-hexylene and, most preferably, methylene and 1,2-ethylene.

r and s are preferably each 0.

R, R' and $R_2$ may preferably each independently of one another be hydrogen or $C_1$–$C_4$alkyl which is unsubstituted or substituted by, typically, halogen, hydroxy, cyano, $C_1$–$C_4$alkoxy, $C_1$–$C_4$alkoxycarbonyl, carboxy, sulfamoyl, sulfo or sulfato. R, R' and $R_2$ are each independently of one another hydrogen or $C_1$–$C_4$alkyl and, most preferably, hydrogen, methyl or ethyl.

U as the radical of a UV absorber may typically be the radical of a 2-(2'-hydroxyphenyl)benzotriazole, 2-hydroxybenzophenone or 2-hydroxyphenyl,1,3,5-triazine, of an oxamide, of an acrylate or of an unsubstituted or substituted benzoic acid or an ester thereof.

U as the radical of a 2-hydroxyphenylbenzotriazole may conveniently be a radical of formula

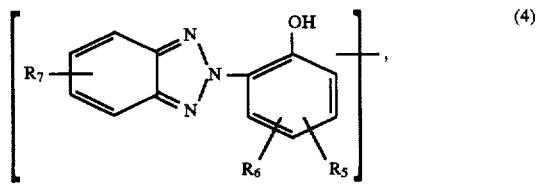

wherein $R_5$ is hydrogen, $C_1$–$C_{12}$alkyl, phenyl-$C_1$–$C_4$alkyl, $C_5$–$C_8$cycloalkyl or a radical of formula

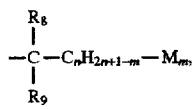

wherein $R_8$ and $R_9$ are each independently of the other alkyl of 1 to 5 carbon atoms, or $R_8$, together with the radical $C_nH_{2n+1-m}$, forms a cycloalkyl radical of 5 to 12 carbon atoms, m is 1 or 2, n is an integer from 2 to 20 and M is a radical of formula —COOR$_{10}$, wherein R$_{10}$ is hydrogen, alkyl of 1 to 12 carbon atoms, alkoxyalkyl containing 1 to 20 carbon atoms in the alkyl and alkoxy moiety respectively, or phenylalkyl containing 1 to 4 carbon atoms in the alkyl moiety, $R_6$ is hydrogen, sulfo, halogen, alkyl of 1 to 18 carbon atoms, phenylalkyl containing 1 4 carbon atoms in the alkyl moiety, and $R_7$ is hydrogen, sulfo, chloro, alkyl or alkoxy of 1 to 4 carbon atoms, or —COOR$_{10}$, wherein R$_{10}$ has the given meaning, and at least one of the radicals $R_5$ and $R_6$ is different from hydrogen.

Illustrative examples of suitable UV absorber radicals U of formula (4) are the radical of 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)- 5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl) benzotriazole, 2-(2'-hydroxy-4'-octyloxyphenyl) benzotriazole, 2-(3',5'-di-tert-amyl-2'-hydroxyphenyl) benzotriazole, 2-(3',5'-bis-(α,α-dimethylbenzyl)-2'-hydroxyphenyl)benzotriazole, mixture of 2-(3'-tert-butyl-2'-hydroxy-5'-(2-octyloxycarbonylethyl)phennyl)-5-chlorobenzotriazole, 2-(3'-tert-butyl-5'-[2-(2-ethylhexyloxy)carbonylethyl]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl) phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, and 2-(3'-tert-butyl-2'-hydroxy-5'-(2-isooctyloxycarbonylethyl) phenylbenzotriazole, 2,2'-methylenebis[4-(1,1,3,3-tetramethylbutyl)-6-benzotriazol-2-ylphenol]; transesterification product of 2-[3'-tert-butyl-5'-(2-methoxycarbonylethyl)-2'-hydroxyphenyl]benzotriazole with polyethylene glycol 300, 2-(2'-hydroxy-5'-sulfophenyl) benzotriazole, 2-(2'-hydroxy-5'-methylphenyl)-5-sulfobenzotriazole, or of 2-(2'-hydroxy-5'-tert-butylphenyl) -5-sulfobenzotriazole.

U as the radical of a 2-hydroxyphenylbenzotriazole is most preferably a radical of formula

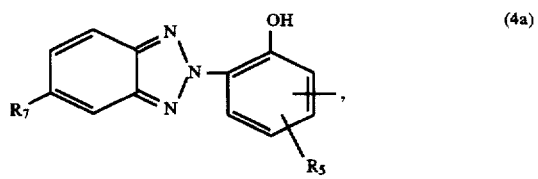

wherein $R_5$ is hydrogen, $C_1$–$C_4$alkyl or sulfo, and $R_7$ is hydrogen, sulfo or carboxy, and wherein one of $R_5$ and $R_7$ is different from hydrogen.

U as the radical of a 2-hydroxyphenyltriazine is conveniently a radical of formula

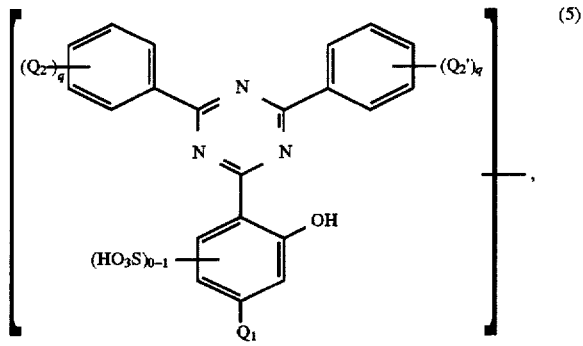

wherein q is an integer from 1 to 3, and $Q_1$, $Q_2$ and $Q_2'$ are each independently of one another hydrogen, hydroxyl, alkyl of 1 to 12 carbon atoms, alkoxy of 1 to 18 carbon atoms, or unsubstituted or hydroxy-substituted $C_1$–$C_4$alkoxy-$C_1$–$C_4$alkoxy.

Illustrative examples of suitable 2-hydroxyphenyltriazine radicals U are the radical of 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propoxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-[2-hydroxy-4-(2-hydroxy-3-butoxypropoxy)phenyl]-4,6-bis(2,4-dimethylphenyl)-1,3,5-triazine, 2-(2-hydroxy-4-methoxy-6-sulfophenyl)-4,6-bis(phenyl)-1,3,5-triazine or 2-[2-hydroxy-4-(2-hydroxy-3-octyloxypropoxy)phenyl]-4,6-bis(2,4-dimethylphenyl)-1,3,5-triazine.

U as the radical of a 2-hydroxybenzophenone is conveniently a radical of formula

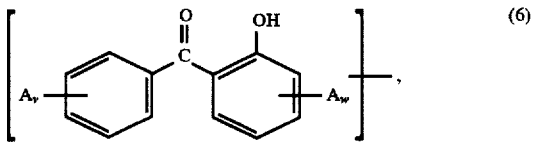

wherein v is an integer from 1 to 3 and w is 1 or 2, and the substituents A are each independently of one another hydrogen, halogen, hydroxyl, sulfo, alkoxy of 1 to 12 carbon atoms or phenyl-$C_1$–$C_4$alkoxy.

Illustrative examples of suitable 2-hydroxybenzophenone radicals U are the radical of 2,4-dihydroxybenzophenone, 2-hydroxy-4-methoxybenzophenone, 2-hydroxy-4-octyloxybenzophenone, 2-hydroxy-4-decyloxybenzophenone, 2-hydroxy-4-dodecyloxybenzophenone, 2-hydroxy-4-methoxy-5-sulfobenzophenone, 2-hydroxy-4-benzyloxybenzophenone, 4,2',4'-trihydroxybenzophenone or 2'-hydroxy-4,4'-dimethoxybenzophenone.

U as the radical of a 2-hydroxybenzophenone is preferably a radical of formula

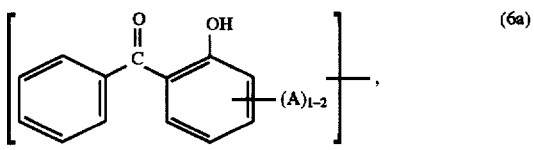

wherein $(A)_{1-2}$ is 1 or 2 identical or different radicals selected from the group consisting of $C_1$–$C_{12}$alkoxy and sulfo.

U as the radical of an oxalanilide is conveniently a radical of formula

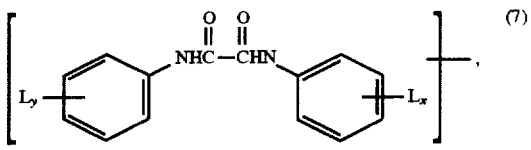

wherein x and y are each independently of the other an integer from 0 to 3, the sum of (x+y) being $\geq 1$, and the L substituents are each independently of one another sulfo or alkyl, alkoxy or allylthio, each of 1 to 22 carbon atoms and each unsubstituted or substituted in the alkyl moiety by sulfo, or phenoxy or phenylthio, each unsubstituted or substituted in the phenyl ring by sulfo.

Typical examples of suitable oxalanilide radicals U are the radical of 4,4'-dioctyloxyoxanilide, 2,2'-diethoxyoxanilide, 2,2'-dioctyloxy-5,5'-di-tert-butyloxanilide, 2,2'-didodecyloxy-5,5'di-tert-butyloxanilide, 2-ethoxy-2'-ethyloxanilide, 2-methoxy- 5-sulfooxanilide, 2-ethoxy-5-sulfooxanilide, 2,5-dimethoxyoxanilide, 2-ethoxy-5-tert-butyl-2'-ethyloxanilide, alone or in admixture with the radical of 2-ethoxy-2'-ethyl-5,4'-di-tert-butyloxanilide, or mixtures of the radicals of o- and p-methoxyanilides and of o- and p-diethoxyoxanilides.

U as oxanilide is preferably a radical of formula

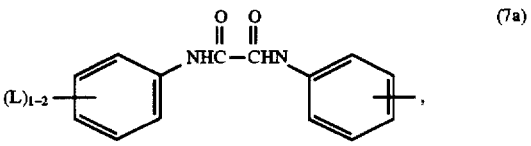

wherein $(L)_{1-2}$ is 1 or 2 radicals L selected from the group consisting of sulfo, $C_1$–$C_4$alkyl and $C_1$–$C_{12}$alkoxy.

Suitable acrylate radicals U are $C_1$–$C_{10}$alkylacrylates which in α-position are unsubstituted or substituted by cyano or carbo-$C_1$–$C_4$alkoxy, in one β-position carry a phenyl, $C_1$–$C_4$alkoxyphenyl or indolinyl radical, and in the other β-position are unsubstituted or substituted by phenyl, $C_1$–$C_4$alkoxyphenyl or $C_1$–$C_4$alkyl.

Typical examples of acrylate radicals U are the radical of ethyl or isooctyl α-cyano-β,β-diphenylacrylate, methyl α-carbomethoxycinnamate, methyl or butyl α-cyano-β-methyl-p-methoxycinnamate, methyl α-carbomethoxy-p-methoxycinnamate or N-(β-carbomethoxy-β-cyanovinyl)-2-methylindoline.

U as the radical of an unsubstituted or substituted benzoic acid or an ester thereof is typically a benzoic acid radical which is unsubstituted or substituted by hydroxy or $C_1$–$C_4$alkyl or the phenyl, $C_1$–$C_8$alkylphenyl or $C_1$–$C_{18}$alkyl ester thereof. Illustrative examples are the radical of benzoic acid, 4-tert-butylphenylsalicylate, phenyl salicylate, octylphenyl salicylate, dibenzoyl resorcinol, bis(4-tert-butylbenzoyl)resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, or 2-methyl-4,6-di-tert-butylphenyl 3,5-di-tert-butyl-4-hydroxybenzoate.

U is preferably a radical of formula (4a), (6a) or (7a) indicated above or the radical of a benzoic acid radical which is unsubstituted or substituted by hydroxy or $C_1$–$C_4$alkyl or the phenyl, $C_1$–$C_8$alkylphenyl or $C_1$–$C_{18}$alkyl ester thereof.

W is preferably a —$NR_2$— radical, wherein $R_2$ has the meanings and preferred meanings given above. The particularly preferred meaning of W is —NH—.

$X_1$ or $X_2$ defined in formula (1) as unsubstituted or substituted amino will be typically understood as meaning —NH$_2$, N-mono- or N,N-di-C$_1$–C$_4$alkylamino, each unsubstituted or substituted in the alkyl moiety by hydroxy, carboxy, sulfo, sulfato or C$_1$–C$_4$alkoxy; cyclohexylamino; or phenylamino or N-C$_1$–C$_4$alkyl-N-phenylamino, each unsubstituted or substituted in the phenyl moiety by C$_1$–C$_4$alkyl, C$_1$–C$_4$alkoxy, carboxy, sulfo, halogen or by a radical of formula

  (8a),

  (8b), wherein Y is vinyl or a radical —CH$_2$—CH$_2$—G, G is a leaving group, and p is an integer from 1 to 6.

Suitable leaving groups G may conveniently be halogen, typically chloro, acyloxy, typically acetoxy or benzoyloxy, phosphato, sulfato and thiosulfato.

Illustrative examples of suitable radicals Y are accordingly vinyl, β-bromoethyl and β-chloroethyl, β-acetoxyethyl, β-benzoyloxyethyl, β-phosphatoethyl, β-sulfatoethyl and β-thiosulfatoethyl. Y is preferably vinyl or β-sulfatoethyl.

p is preferably 2, 3 or 4 and is most preferably 2 or 3.

X$_1$ and X$_2$ defined as unsubstituted or substituted amino are each independently of the other amino, methylamino, ethylamino, carboxymethylamino, β-hydroxyethylamino, β-sulfoethylamino, N,N-di-β-hydroxyethylamino, cyclohexylamino, o-, m- or p-methylphenylamino, o-, m- or p-methoxyphenylamino, o-, m- or p-sulfophenylamino, 2,4- or 2,5-disulfophenylamino, o-carboxyphenylamino, N-ethyl-N-phenylamino, N-methyl-N-phenylamino, or phenylamino which is substituted by a radical of formula (8a) or (8b). Most preferably, X$_1$ and X$_2$ as unsubstituted or substituted amino are each independently of the other amino, β-sulfoethylamino, β-hydroxyethylamino, N,N-di-β-hydroxyethylamino and o-, m- or p-sulfophenylamino.

Preferred meanings of X$_1$ and X$_2$ are each independently of the other chloro, fluoro, hydroxy, amino, N-mono- or N,N-di-C$_1$–C$_4$alkylamino, each unsubstituted or substituted in the alkyl moiety by hydroxy, sulfo or sulfato, or phenylamino which is unsubstituted or substituted in the phenyl moiety by, typically, methyl, ethyl, methoxy, ethoxy, carboxy, sulfo, chloro or by a radical of formula (8a) or (8b).

Most preferably, X$_1$ and X$_2$ are each independently of the other chloro or fluoro.

T in the significance of an alkoxy radical is preferably a C$_1$–C$_4$alkoxy radical, typically methoxy, ethoxy, n- or isopropoxy or n-, iso-, sec- or tert-butoxy. The preferred meanings are methoxy and isopropoxy.

T in the significance of an aryloxy radical is typically unsubstituted or substituted phenoxy, possible substituents being C$_1$–C$_4$alkyl, C$_1$–C$_4$alkoxy, halogen, hydroxy, carboxy or sulfo.

T defined as an alkylthio radical is typically C$_1$–C$_4$alkylthio and, preferably, methylthio or ethylthio.

T defined as an arylthio radical is typically unsubstituted or substituted phenylthio, possible substituents being C$_1$–C$_4$alkyl, C$_1$–C$_4$alkoxy, halogen, hydroxy, carboxy or sulfo.

If T independently has one of the meanings previously given for X$_1$, then the preferred meanings will also in this case apply.

T in the significance of a nitrogen-containing heterocyclic radical will typically be the piperidino or piperazino radical or, preferably, the morpholino radical.

T is preferably unsubstituted or substituted amino, morpholino, C$_1$–C$_4$alkoxy or a radical —W—(B$_1$)$_r$—(W$_1$)$_s$—(B$_2$)$_r$—U, wherein W, W$_1$, B$_1$, B$_2$, U, r, s and t have the meanings and preferred meanings previously assigned to them.

T is more particularly a radical —W—(B$_1$)$_r$—U, wherein W, B$_1$, U and t have the meanings and preferred meanings previously assigned to them, or are amino, methylamino, ethylamino, carboxymethylamino, β-hydroxyethylamino, β-sulfoethylamino, N,N-di-β-hydroxyethylamino, cyclohexylamino, o-, m- or p-methylphenylamino, o-, m- or p-methoxyphenylamino, o-, m- or p-sulfophenylamino, 2,4- or 2,5-disulfophenylamino, o-carboxyphenylamino, N-ethyl-N-phenylamino, N-methyl-N-phenylamino, or phenylamino which is substituted by a radical of formula (8a) or (8b) as shown above.

Most preferably, T is a radical —W—(B$_1$)$_r$—U, wherein W, B$_1$, U and t have the meanings and preferred meanings previously assigned to them.

A preferred embodiment of this invention relates to compounds of formula

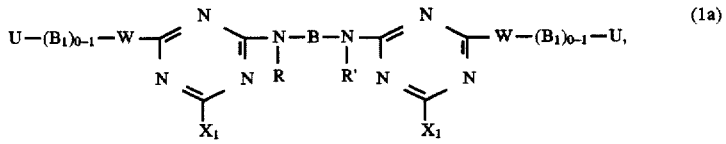  (1a)

wherein B is 4-sulfo-1,3-phenylene, 3-sulfo-1,4-phenylene, 3,6-disulfo-1,4-phenylene or 4,6-disulfo-1,3-phenylene, B$_1$ is straight-chain or branched C$_1$–C$_6$alkylene, R and R' are each independently of the other hydrogen, methyl or ethyl, W is the —NH— group, X$_1$ and X$_2$ are each chloro or fluoro, and U is (i) a radical of formula

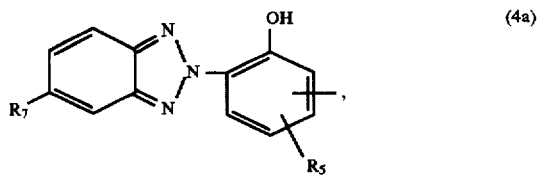  (4a)

wherein R$_5$ is hydrogen, C$_1$–C$_4$alkyl or sulfo and R$_7$ is hydrogen, sulfo or carboxy, and wherein one of R$_5$ and R$_7$ is different from hydrogen;

(ii) a radical of formula

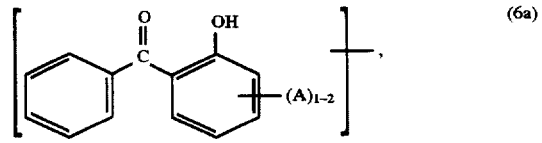  (6a)

wherein (A)$_{1-2}$ is 1 or 2 identical or different radicals selected from the group consisting of C$_1$–C$_{12}$alkoxy and sulfo;

(iii) a radical of formula

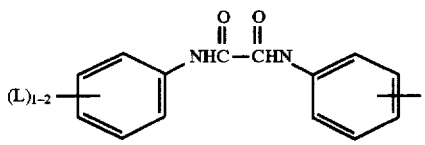

wherein $(L)_{1-2}$ is 1 or 2 radicals L selected from the group consisting of sulfo, $C_1$–$C_4$alkyl and $C_1$–$C_{12}$alkoxy; or (iv) an unsubstituted or hydroxy- or $C_1$–$C_4$alkyl-substituted benzoic acid radical or the phenyl, $C_1$–$C_8$alkylphenyl or $C_1$–$C_{18}$alkyl ester thereof.

A particularly preferred embodiment of this invention relates to compounds of formula (1a) shown above, wherein B, $B_1$, R, R', W and $X_1$ are as defined in connection with formula (1a) and U is a radical of formula (7a) above.

In formulae (1) to (8b), $C_1$–$C_{18}$alkyl will typically be methyl, ethyl, n- or isopropyl, n-, iso-, sec- or tert-butyl or straight-chain or branched heptyl, octyl, nonyl, decyl, undecyl, dodecyl, tridecyl, tetradecyl, pentadecyl, hexadecyl, heptadecyl or octadecyl. $C_1$–$C_{18}$Alkoxy will typically be taken to mean methoxy, ethoxy, n- or isopropoxy, n-, iso-, sec- or tert-butoxy or or straight-chain or branched pentoxy, hexyloxy, heptyloxy, octyloxy, nonyloxy, decyloxy, undecyloxy, dodecyloxy, tridecyloxy, tetradecyloxy, pentadecyloxy, hexadecyloxy, heptadecyloxy or octadecyloxy. $C_1$–$C_{12}$Alkylene is typically methylene, 1,1- or 1,2-ethylene, 1,2- or 1,3-propylene or straight-chain or branched butylene, pentylene, hexylene, heptylene, octylene, nonylene, decylene, undecylene or dodecylene. Halogen will be typically understood as meaning fluoro, chloro or bromo. $C_1$–$C_4$Alkoxycarbonyl will typically be taken to mean methoxycarbonyl, ethoxycarbonyl, n- or isopropoxycarbonyl or n-, iso-, sec- or tert-butoxycarbonyl. $C_1$–$C_4$Alkylthio is exemplified by methylthio or ethylthio. $C_5$–$C_8$Cycloalkyl is typically cyclopentyl or, preferably, cyclohexyl.

The compounds of formula (1) must carry at least one group which is removable with alkali, i.e. they carry at least one halogen atom at a triazinyl radical or a radical of formula (8a) or (8b) above.

The compounds of formula (1) must further carry at least one sulfo or sulfato group, in which case these compounds can be obtained in the form of the free acid or, preferably, in salt form, typically as sodium, lithium, potassium or ammonium salt.

The compounds of formula (1) are fibre-reactive. By fibre-reactive radicals are meant those radicals that are able to react with the hydroxyl groups of cellulose, with the amino, carboxyl, hydroxyl and thiol groups of wool and silk, or with the amino and, where present, carboxyl groups of synthetic polyamides to form covalent chemical bonds.

The compounds of formula (1) may conveniently be prepared by reacting a compound of formula $$U-(B_2)_r-(W_1)_s-(B_1)_t-W-H \quad (8)$$

a compound of formula $$H-RN-B-NR'-H \quad (9),$$

a compound of formula

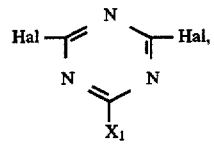

a compound of formula

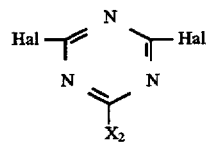

optionally a compound of formula $$T^*-H \quad (11),$$

wherein U, B, $B_1$, $B_2$, W, $W_1$, R, R', $X_1$, $X_2$, r, s and t are each as previously defined, Hal is halogen, preferably fluoro or chloro, and T* has the meaning previously given for T, except halogen, with one another, and the sequence of the partial reactions may be freely chosen having regard to the starting compounds.

A variant of the process in the case that r and s are each 0, T is a radical —W—$(B_1)_t$—U and $X_1$ and $X_2$ are identical, consists in reacting c. 1 molar equivalent of a compound of formula $$U-(B_1)_t-W-H \quad (8')$$

initially with c. 1 molar equivalent of a compound of formula

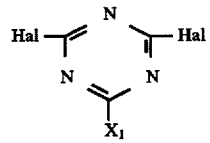

and subsequently reacting the primary condensate with c. 0.5 molar equivalent of a diamine of formula $$H-RN-B-NR'-H \quad (9)$$

wherein Hal, $X_1$, R, R', B, U, $B_1$, W and t each have the meanings previously assigned to them.

Another variant of the process for the case that r and s are each 0 and T is a radical —W—$(B_1)_t$—U, consists in reacting c. 2 molar equivalents of a compound of formula $$U-(B_1)_t-W-H \quad (8')$$

with c. 1 molar equivalent of a compound of formula

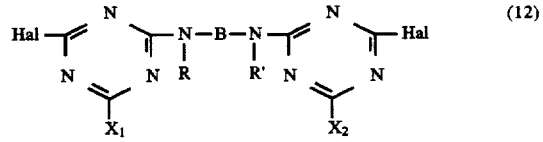

wherein Hal, $X_1$, $X_2$, R, R', B, U, $B_1$, W and t each have the meanings previously assigned to them.

The conditions to be used in the condensation of the compounds of formula (8), (9) and (11) with a halotriazine are well known in the field of the chemistry of reactive dyes. This reaction is usually carried out in aqueous or aqueous-organic medium in the presence of an acid acceptor, conveniently sodium carbonate or sodium hydroxide.

The compounds of formula (9), (10a), (10b), (11) and (12) are known or can be obtained by per se known methods.

The UV absorbers of formula (8) and (8') belong to known classes of compounds and can be prepared in per se known manner, conveniently as disclosed in U.S. Pat. No. 3,041, 330, U.S. Pat. No. 3,042,669 or U.S. Pat. No. 3,159,646.

The novel UV absorbers of formula (1) are suitable for the photochemical stabilisation of undyed and dyed or printed fibre materials, typically of silk, leather, wool, polyamide or polyurethanes, and, in particular, of cellulosic fibre materials of all kinds. Such fibre materials are typically the natural cellulose fibres such as cotton, linen, jute and hemp, as well as cellulose and regenerated cellulose. Cotton textile fabrics are preferred. The compounds of formula (1) are also suitable for the photochemical stabilisation of hydroxyl group-containing fibres that are components of fibre blends, e.g. blends of cotton and polyester or polyamide fibres. A further preferred field of use relates to the blocking or lessening of UV radiation passing through said textile fabrics (UV cutting) and the increased sun protection that textile fabrics treated with a compound of this invention afford the human skin.

This end is achieved by applying one or more than one compound of formula (1), advantageously in an amount of 0.01 to 5% by weight, preferably 0.1 to 3% by weight and, most preferably, 0.25 to 2% by weight, based on the weight of the fibre material, to the textile material by a conventional dyeing process for reactive dyes. If the textile fabric is a cellulosic material dyed with a reactive dye, then the UV absorber of formula (1) can be applied before, during or after dyeing, preferably simultaneously with the application of the dye.

The compounds of formula (1) can be applied to the fibre material and fixed thereon in different manner, preferably in the form of aqueous solutions or print pastes. They are suitable for the exhaust process as well as for pad dyeing. They can be used at low temperature and require only short steaming times in pad-steam processes. Fixation is excellent and non-fixed absorber can be easily washed off, the difference between degree of exhaustion and percentage fixation being remarkably small. The compounds of formula (1) are also suitable for printing, especially on cotton.

The textile materials treated with the compounds of formula (1) have enhanced protection against photochemical fibre degradation and yellowing as well as, in the case of dyed material, enhanced fastness to hot light. The strongly enhanced light stability of the treated textile fabric is to be particularly highlighted and is seen in the fact that, compared with untreated fabric, textile fabric treated with a compound of formula (1) has a greatly enhanced sun protection factor (SPR).

The sun protection factor is defined as the quotient of harmful UV radiation without sun protection and harmful UV radiation with sun protection. Accordingly, a sun protection factor is also an indicator of the permeability of the untreated fabric and the fabric treated with a compound of formula (1) to UV radiation. The calculation of the sun protection factor of textile fabrics is explained, inter alia, in WO 94/04515 or in J. Soc. Cosmet. Chem. 40, 127–133 (1989) and can be determined in analogous manner.

The invention is illustrated by the following Examples in which parts and percentages are by weight, unless otherwise indicated.

EXAMPLE 1

A mixture of 334 parts of 2-(2'-hydroxy-5'-tert-butylphenyl)benzotriazole and 193 parts of N-hydroxymethylchloroacetamide is added at room temperature to 1380 parts of 98% sulfuric acid. The reaction mixture is stirred for c. 3 hours at room temperature and then poured onto a mixture of ice/water. The precipitate of the compound of formula

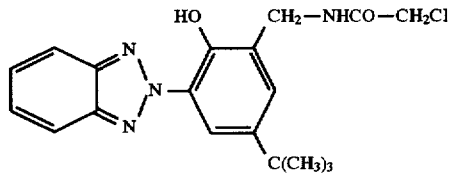

is isolated by filtration, washed with water and dried.

EXAMPLE 2

A solution of 223 parts of the benzotriazole obtained according to Example 1 is kept for c. 20 hours in 745 parts of 100% sulfuric acid at a temperature of 80°–82° C. and a pressure of c. 130 mbar. The reaction mixture is then cooled and poured onto a mixture of ice/water. Then 45 parts of silica gel are added, the batch is stirred for c. 30 minutes at 40° C. and clarified by filtration. The filtrate is heated for c. 3.5 hours to 95° C. The precipitate that settles out of the cooled filtrate and which contains the compound of formula

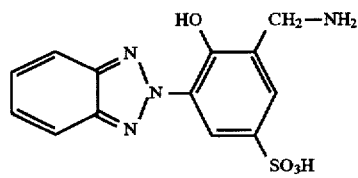

is isolated by filtration and washed with water.

For purification, the solid is stirred in 1000 parts of water at a temperature of 35° C. and the pH is adjusted to 11 with conc. sodium hydroxide solution. Silica gel is added, the batch is heated to c. 80° C., and the insoluble residue is collected by hot filtration and washed with hot water. The filtrate is acidified with 50% sulfuric acid (Congo red test) to precipitate the product, which is then isolated by filtration, washed with water until neutral and dried.

The crude product is taken up in water/N,N-dimethylformamide/dioxane and dissolved by addition of 30% ammonia. The product is afterwards precipitated once more by slowly adding 4N hydrochloric acid. The precipitate is isolated by filtration, washed with water and dried under vacuum.

EXAMPLE 3

6.4 parts of the sulfonated benzotriazole obtained according to Example 2 are dissolved in 200 parts of water and 140 parts of dimethoxyethane by adding 10 parts of 2N sodium hydroxide solution, and then 5.6 parts of the compound of formula

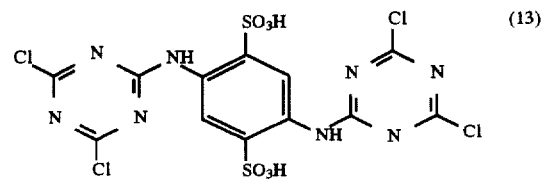

(prepared in accordance with DE-OS 2 105 309, Example 2) are added over c. 2 hours at a temperature of c. 35° C., while keeping the pH constant at 8.5 by addition of 2N sodium hydroxide solution. After stirring for 30 minutes, the pH is adjusted to 7.5 and stirring is continued for about another 15 hours at 35° C.

The reaction mixture is subsequently clarified by filtration and the compound of formula

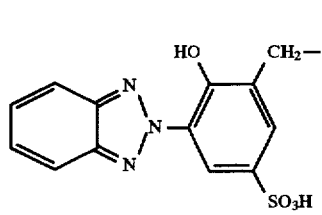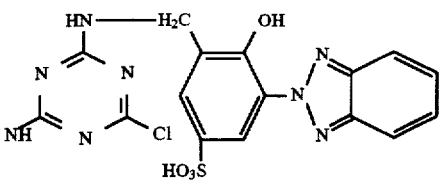

is salted out. When this compound is applied to cotton fabric by a standard method of applying reactive dyes, the treated fabric has an enhanced sun protection factor compared with untreated fabric.

EXAMPLE 4

To a solution of 3 parts of the compound of formula (13) shown in Example 3 in 60 parts of water are added 1.5 parts of 4-aminobenzoic acid and the mixture is stirred while keeping the pH constant at 7 by adding sodium hydroxide solution. When the reaction is complete, the compound of formula

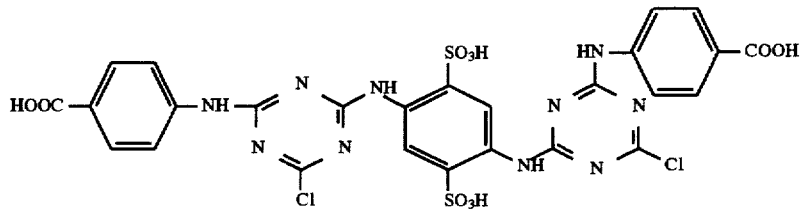

is salted out. When this compound is applied to cotton fabric by a standard method of applying reactive dyes, the treated fabric has an enhanced sun protection factor compared with untreated fabric.

EXAMPLE 5

A mixture of 20 parts of ethyl 3-nitrooxanilate and 23 parts of o-phenetidine is heated for 4 hours under nitrogen to 140°–150° C. Afterwards the pressure is reduced to c. 40 mbar and the mixture is stirred for a further 4 hours at c. 140° C. The mixture is then cooled, and water and 4N hydrochloric acid are added to the semi-solid residue. The compound of formula

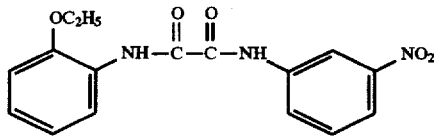 (14)

is isolated by filtration, washed with water and dried.

EXAMPLE 6

9.9 parts of the compound of formula (14) according to Example 5 are added to 55 parts of 100% sulfuric acid over 1 hour, while keeping the temperature below 20° C. The batch is stirred for 1 hour and then poured onto ice. After addition of sodium chloride the solid is isolated by filtration, then taken up in a solution of sodium chloride, and the product of formula

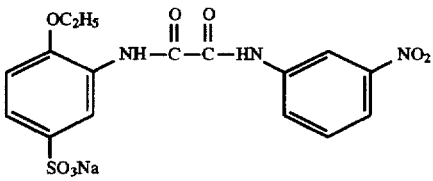

is obtained by treatment with sodium hydroxide solution.

EXAMPLE 7

A suspension of 12 parts of the nitro compound obtained according to Example 6 in 1000 ml of water is subjected to catalytic hydrogenation using a Pd/C (5%) catalyst, and the resultant compound of formula

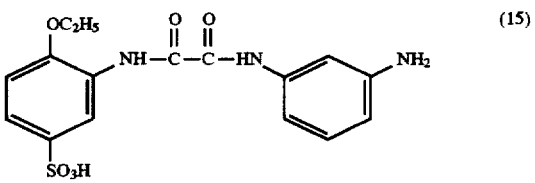 (15)

is then isolated and purified in conventional manner.

EXAMPLE 8

To a suspension of 2.9 parts of the copmpound of formula (13) obtained according to Example 3 in 75 parts of water are added 4 parts of the oxanilide component obtained according to Example 7. The reaction mixture is heated gradually to 35° C., while keeping the pH constant at 7 by the dropwise addition of sodium hydroxide solution. When the condensation is complete, the reaction mixture is freed from salt by dialysis and lyophilised, giving the compound of formula

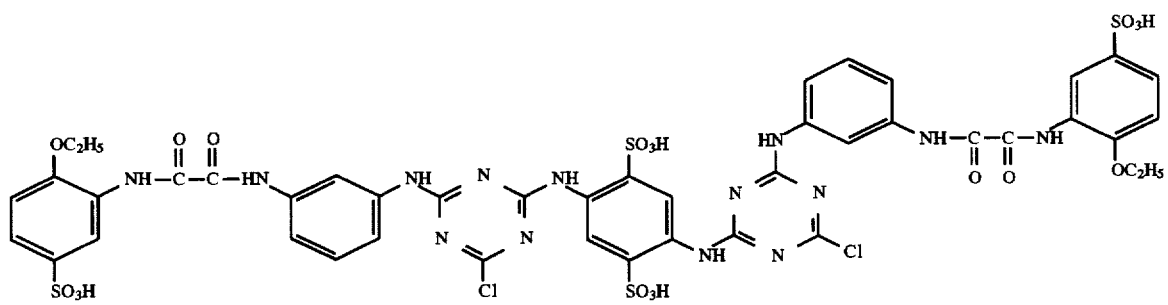

as a powder. When this compound is applied to cotton fabric by a standard method of applying reactive dyes, the treated fabric has an enhanced sun protection factor compared with untreated fabric.

EXAMPLE 9

2 parts of 100% sulfuric acid are added to a suspension of 9.1 parts of the compound of formula (15) according to Example 7 in 45 parts of sulfolane, and the pressure in the reactor is reduced to 200 mbar. The reaction mixture is afterwards heated for 4 hours to 190° C., then cooled to room temperature. After addition of ethanol, the solid is isolated from the resultant suspension and washed well with ethanol, giving the compound of formula

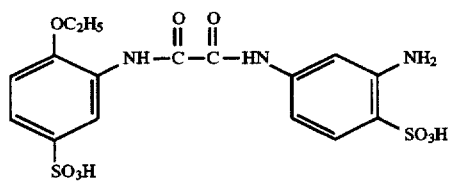 (16)

as a powder.

EXAMPLES 10–12

The following oxanilides can be obtained in general accordance with the procedures described in Examples 5–7 and 9:

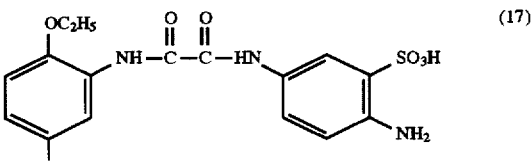 (17)

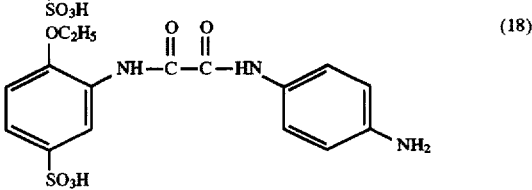 (18)

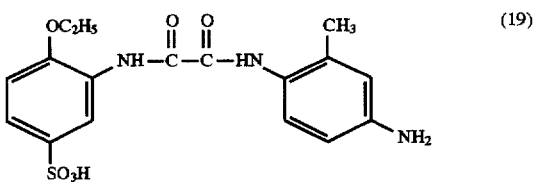 (19)

EXAMPLES 13–16

In general accordance with the procedure described in Example 8, the following fibre-reactive UV absorbers can be prepared using the compounds of (16) to (19) obtained according to Examples 9–12:

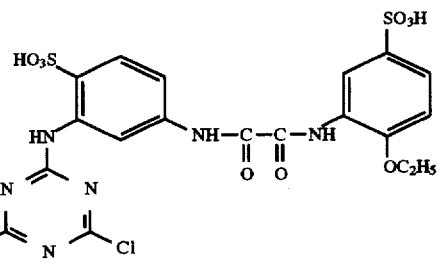

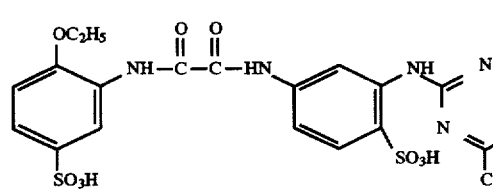

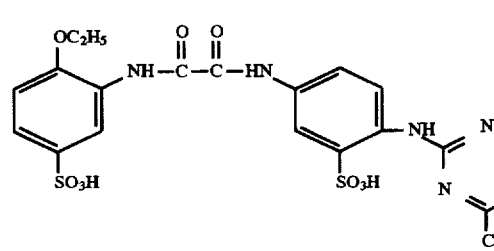

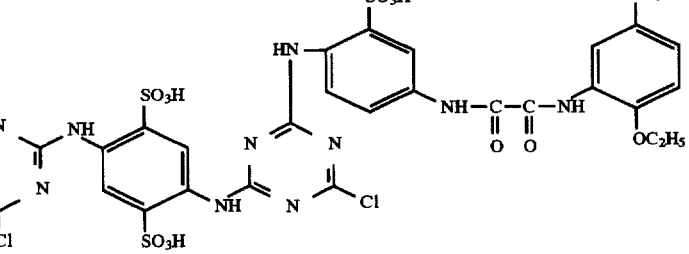

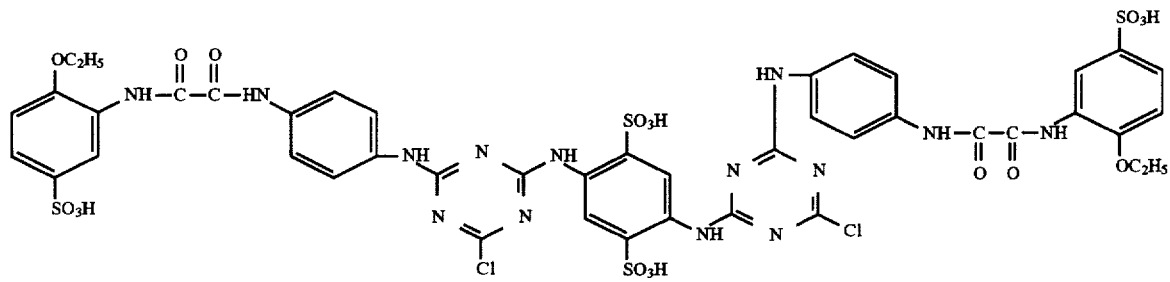

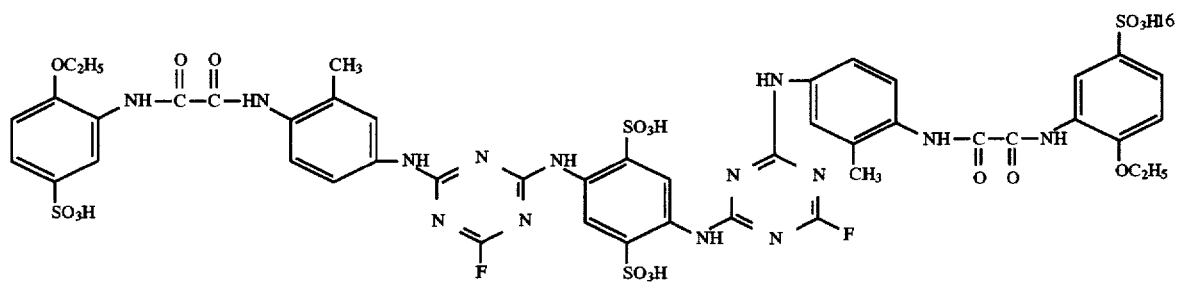

EXAMPLE 17

A neutralised solution of 6.1 parts of the compound of formula (16) according to Example 9 in 30 parts of water is added dropwise to a dispersion of 2.4 parts of cyanuric chloride in 10 parts of water and 15 parts of ice, while keeping the pH constant at c. 4.5 by the simultaneous dropwise addition of dilute sodium hydroxide solution. When the second condensation is complete, the reaction mixture is clarified by filtration and the product of formula

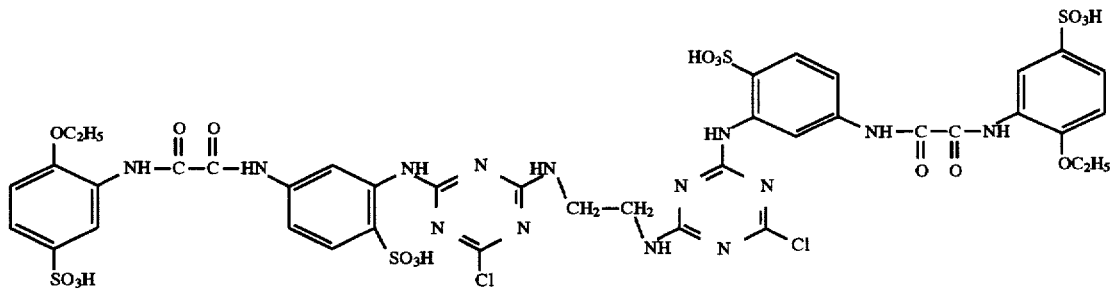

is salted out with sodium chloride.

EXAMPLES 18–19
The following compounds can be prepared in general accordance with the procedure described in Example 17:
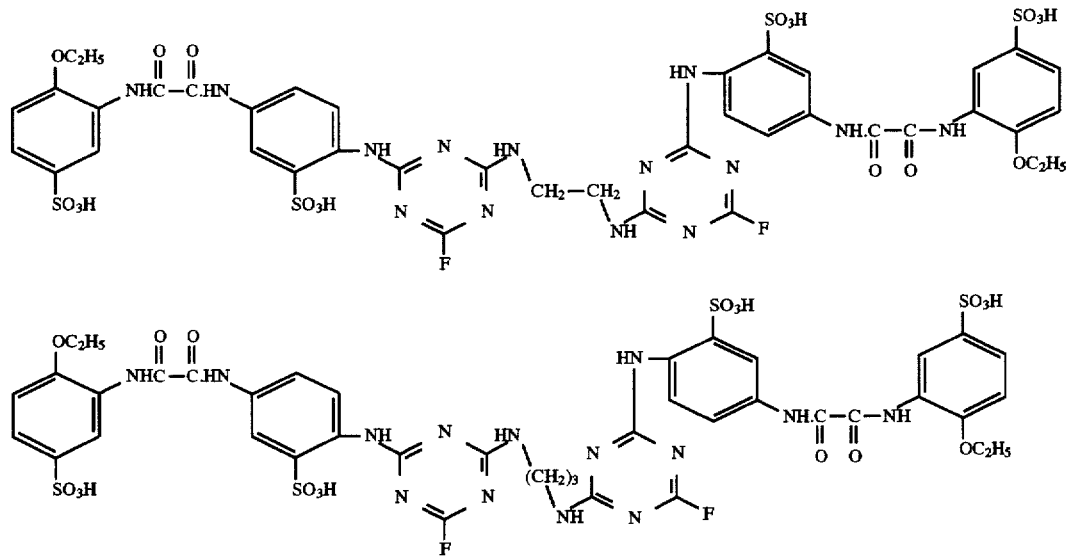
EXAMPLES 20–22
The following compounds can be prepared in general accordance with the procedure described in Example 8:
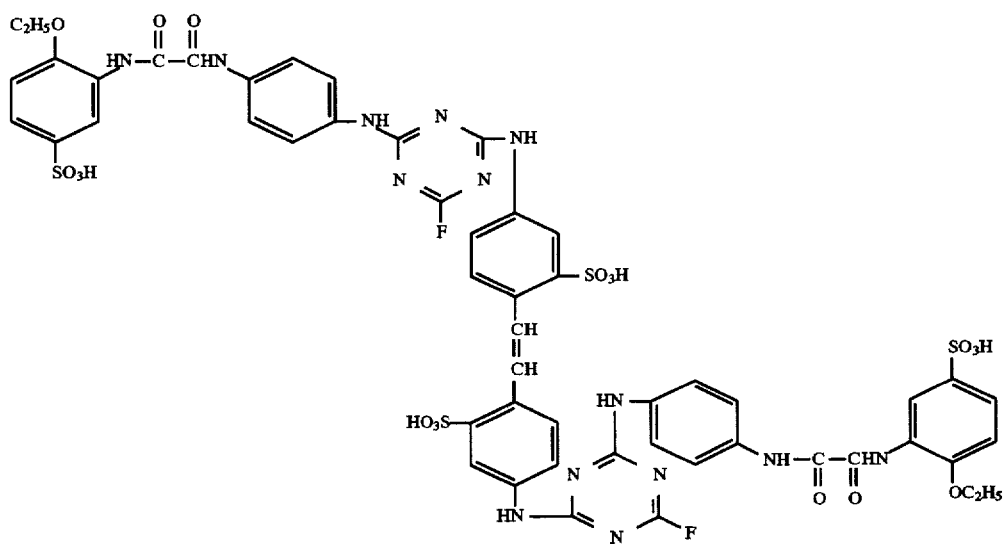

-continued

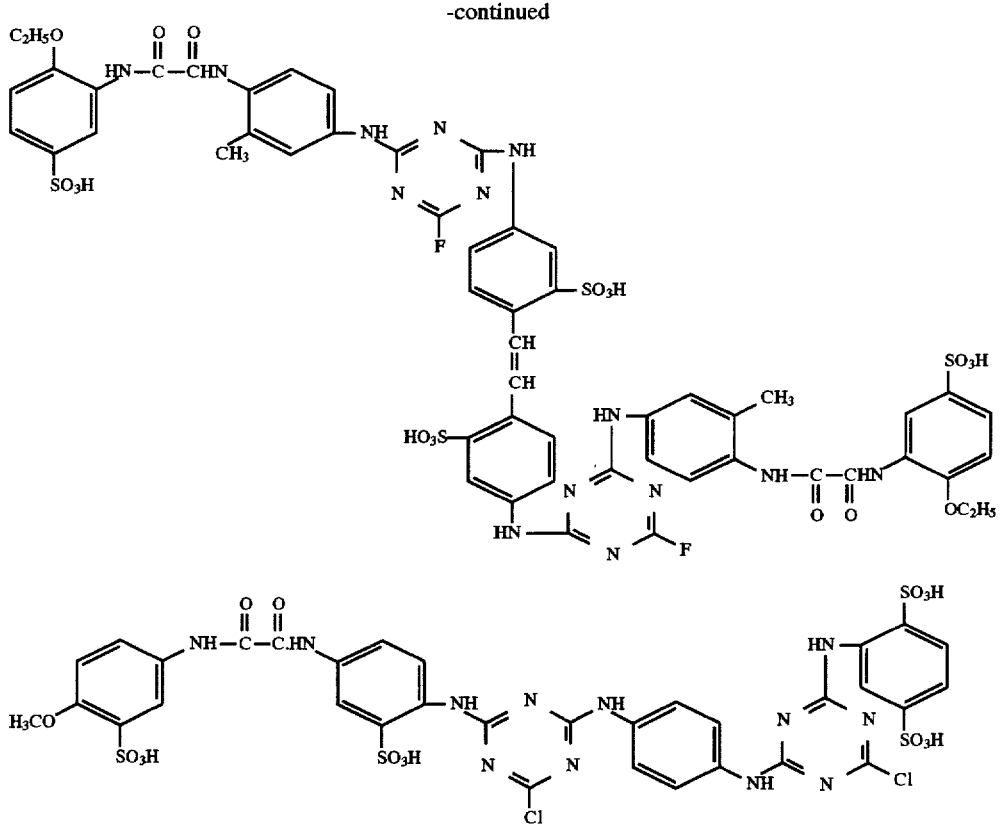

APPLICATION EXAMPLE

In a jet dyeing apparatus, 100 g of a bleached cotton tricot fabric are treated for 20 minutes at 60° C. with a liquor containing 1 g of the compound of Example 8 and 75 g of sodium sulfate at a liquor to goods ratio of 1:15. After addition of 30 g of sodium carbonate, the cotton tricot is treated for a further 60 minutes. The fabric is then removed from the liquor, washed repeatedly with cold, warm and hot water and dried. The treated cotton tricot fabric has an excellent sun protection factor.

What is claimed is:

1. A compound of formula

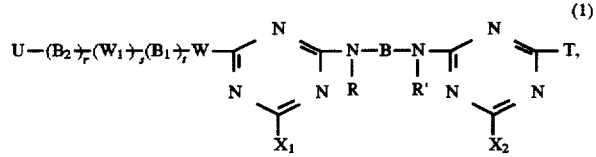

wherein

B is an aliphatic, cycloaliphatic, aromatic or aromatic-aliphatic linking group or, together with —NR— and —NR'—, forms a heterocyclic ring, $B_1$ and $B_2$ are each independently of the other an aliphatic linking group, R, R' and $R_2$ are each independently of one another hydrogen or unsubstituted or substituted $C_1$–$C_4$alkyl, U is the radical of an oxamide-UV absorber of the formula

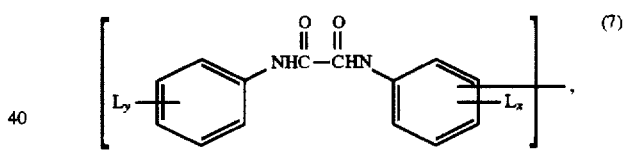

wherein x and y are each independently of the other an integer from 0 to 3, the sum of (x+y) being greater than or equal to 1, and the L substituents are each independently of one another sulfo or alkyl, alkoxy or alkylthio, each of 1 to 22 carbon atoms and each unsubstituted or substituted in the alkyl moiety by sulfo, or phenoxy or phenylthio, each unsubstituted or substituted in the phenyl ring by sulfo, W is —$NR_2$—, $W_1$ is a radical —C(O)O—, —O(O)C—, —C(O)NH— or —HN(O)C—, $X_1$ and $X_2$ are each independently of the other halogen, hydroxy, unsubstituted or substituted amino, 3-carboxypyridin-1-yl or 3-carbamoylpyridin-1-yl, T independently has one of the meanings given for $X_1$ or is an alkoxy, aryloxy, alkylthio or arylthio radical which may be further substituted or is a nitrogen containing heterocyclic radical or is independently a radical U—$(B_2)_r$—$(W_1)_s$—$(B_1)_t$—W—, wherein U, $B_1$, $B_2$, W and $W_1$ are each as defined above, and r, s and t are each independently of one another 0 or 1, and s is 0 when t is 0, with the proviso that the compounds of formula (1) contain at least one sulfo or sulfato group and at least one group which is removable under alkaline conditions.

2. A compound according to claim 1 wherein U is a radical of formula

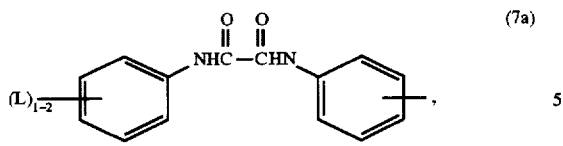

wherein (L)$_{1-2}$ is 1 or 2 radicals L selected from the group consisting of sulfo, $C_1$–$C_4$alkyl and $C_1$–$C_{12}$alkoxy.

3. A compound according to claim 1 of formula

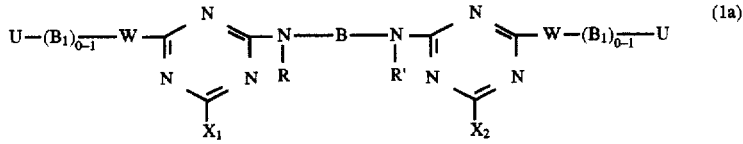

wherein B is 4-sulfo-1,3-phenylene, 3-sulfo-1,4-phenylene, 3,6-disulfo-1,4-phenylene or 4,6-disulfo-1,3-phenylene, $B_1$ is straight-chain or branched $C_1$–$C_6$alkylene, R and R' are each independently of the other hydrogen, methyl or ethyl, W is the —NH— group, $X_1$ and $X_2$ are each chloro or fluoro, and U is a radical of formula

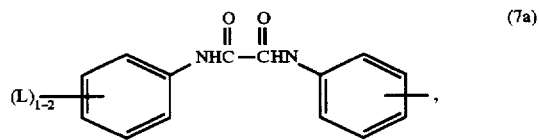

wherein (L)$_{1-2}$ is 1 or 2 radicals L selected from the group consisting of sulfo, $C_1$–$C_4$alkyl and $C_1$–$C_{12}$alkoxy.

4. A compound according to claim 1, wherein r and s are each 0.

5. A compound according to claim 1, wherein B is $C_2$–$C_6$alkylene which is unsubstituted or substituted by hydroxy, sulfo or sulfato, or 1,3- or 1,4-phenylene, each unsubstituted or substituted by sulfo, carboxy, chloro, methyl or methoxy, naphthylene which is substituted by 1 or 2 sulfo groups, or is a radical of formula

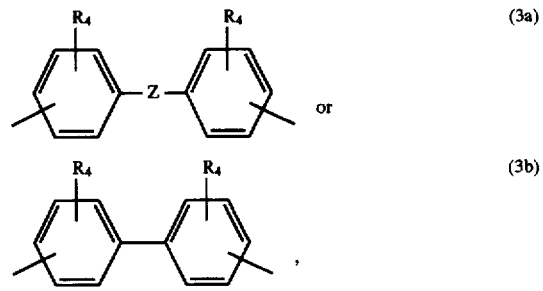

wherein Z is —NHCONH—, —O—, —NH—, —CH=CH— or —CH$_2$—, and $R_4$ is hydrogen or sulfo.

6. A compound according to claim 1, wherein B is 4-sulfo-1,3-phenylene, 3-sulfo-1,4-phenylene, 3,6-disulfo-1,4-phenylene or 4,6-disulfo-1,3-phenylene.

7. A compound according to claim 1, wherein $B_1$ is straight-chain or branched $C_1$–$C_6$alkylene.

8. A compound according to claim 1, wherein R and R' are each independently of the other hydrogen or $C_1$–$C_4$alkyl, and $X_1$ and $X_2$ are each chloro or fluoro.

9. A compound according to claim 1, wherein W is a —NR$_2$— radical and $R_2$ is hydrogen or $C_1$–$C_4$alkyl.

10. A compound according to claim 1, wherein T is unsubstituted or substituted amino, morpholino, $C_1$–$C_4$alkoxy, or is a radical —W—(B$_1$)$_r$—(W$_1$)$_s$—(B$_2$)$_r$—U.

11. A compound according to claim 1, wherein T is amino, methylamino, ethylamino, carboxymethylamino, β-hydroxyethylamino, β-sulfoethylamino, N,N-di-β-hydroxyethylamino, cyclohexylamino, o-, m- or p-methylphenylamino, o-, m- or p-methoxyphenylamino, o-, m- or p-sulfophenylamino, 2,4- or 2,5-disulfophenylamino, o-carboxyphenylamino, N-ethyl-N-phenylamino, N-methyl-N-phenylamino, or phenylamino which is substituted by a radical of formula —SO$_2$—Y  (8a), —CONH—(CH$_2$)$_p$—SO$_2$—Y  (8b), wherein Y is vinyl or a radical —CH$_2$—CH$_2$—G, G is a leaving group, and p is an integer from 1 to 6.

12. A compound of the formula (1) according to claim 1, wherein T is a radical —W—(B$_1$)$_r$—U and r and s are each 0.

* * * * *